United States Patent [19]
Ratcliff et al.

[11] Patent Number: 5,800,445
[45] Date of Patent: Sep. 1, 1998

[54] TISSUE TAGGING DEVICE

[75] Inventors: Keith Ratcliff, Newtown; Salvatore Castro, Seymour; Robert C. Savage, Stratford, all of Conn.; Jude S. Sauer, Pittsford, N.Y.; Roger J. Greenwald, Holley, N.Y.; Mark A. Bovard, Palmyra, N.Y.

[73] Assignee: United States Surgical Corporation, Norwalk, Conn.

[21] Appl. No.: 546,011

[22] Filed: Oct. 20, 1995

[51] Int. Cl.⁶ ............................................. A61B 17/00
[52] U.S. Cl. ............................................. 606/116
[58] Field of Search ........................... 604/116; 606/1, 606/187, 116; 128/749–754

[56] References Cited

U.S. PATENT DOCUMENTS

| | | |
|---|---|---|
| 3,836,776 | 9/1974 | Gullekson . |
| 4,007,732 | 2/1977 | Kvayle et al. . |
| 4,230,123 | 10/1980 | Hawkins, Jr. . |
| 4,235,238 | 11/1980 | Oglio et al. . |
| 4,592,356 | 6/1986 | Gutierrez . |
| 4,669,473 | 6/1987 | Richards et al. . |
| 4,682,606 | 7/1987 | DeCaprio . |
| 4,741,330 | 5/1988 | Hayhurst . |
| 4,774,948 | 10/1988 | Markham . |
| 4,790,329 | 12/1988 | Simon . |
| 4,799,495 | 1/1989 | Hawkins et al. . |
| 4,931,059 | 6/1990 | Markham . |
| 4,966,583 | 10/1990 | Debbas . |
| 4,986,279 | 1/1991 | O'Neill . |
| 5,011,473 | 4/1991 | Gatturna . |
| 5,021,059 | 6/1991 | Kensey et al. . |
| 5,031,634 | 7/1991 | Simon . |
| 5,041,129 | 8/1991 | Hayhurst et al. . |
| 5,059,197 | 10/1991 | Urie et al. . |
| 5,111,828 | 5/1992 | Kornberg et al. . |
| 5,123,914 | 6/1992 | Cope . |
| 5,127,916 | 7/1992 | Spencer et al. . |
| 5,158,084 | 10/1992 | Ghiatas . |
| 5,158,565 | 10/1992 | Marcadis et al. . |
| 5,195,540 | 3/1993 | Shiber . |
| 5,197,482 | 3/1993 | Rank et al. . |
| 5,197,484 | 3/1993 | Kornberg et al. . |
| 5,217,435 | 6/1993 | Kring . |
| 5,221,269 | 6/1993 | Miller et al. . |
| 5,234,426 | 8/1993 | Rank et al. . |
| 5,269,809 | 12/1993 | Hayhurst et al. . |

(List continued on next page.)

FOREIGN PATENT DOCUMENTS

| | | |
|---|---|---|
| 481 685 A1 | 4/1992 | European Pat. Off. . |
| WO 9309720 | 5/1993 | European Pat. Off. . |
| 2919-009 | 11/1979 | Germany . |
| 4216694 A1 | 12/1992 | Germany . |
| WO 86/05378 | 9/1986 | WIPO . |

OTHER PUBLICATIONS

Duh et al., "New Laparoscopic Placement of Gastronomy & Jejunostomy Feeding Tubes", (Jun. 1993 4 pgs.).
Duh et al., "Laparoscopic Gastronomy Using T–fasteners as Retractors and Anchors", (1993, pp. 60–63).
C. Cope et al., "Cope Gastrointestinal Suture Anchor Sets", (1992, 4 pgs.).
Acufex Microsurgical, Inc. Product Brochure, 1994.

*Primary Examiner*—Glenn K. Dawson

[57] ABSTRACT

A tagging device for marking the location of lesions within the body prior to a surgical procedure such as excision or biopsy. The device includes an elongated tube having one end supported on a housing and a second end extending distally therefrom. An anchor is positioned within the distal end of the elongated tube and has an elongated member extending proximally therefrom. An actuation assembly including a plunger is movable within the tube to engage and push the anchor from the distal end of the tube. The anchor and the actuation assembly are positioned and configured such that the anchor is pivoted from a position parallel to the longitudinal axis of the tube to a position perpendicular to the longitudinal axis of the tube as it as being pushed from the tube.

22 Claims, 12 Drawing Sheets

U.S. PATENT DOCUMENTS

| | | |
|---|---|---|
| 5,301,682 | 4/1994 | Debbas . |
| 5,353,804 | 10/1994 | Kornberg et al. . |
| 5,409,004 | 4/1995 | Sloan . |
| 5,417,691 | 5/1995 | Hayhurst . |
| 5,445,645 | 8/1995 | Debbas . |
| 5,470,337 | 11/1995 | Moss ........................................ 606/187 |
| 5,488,958 | 2/1996 | Topel et al. . |

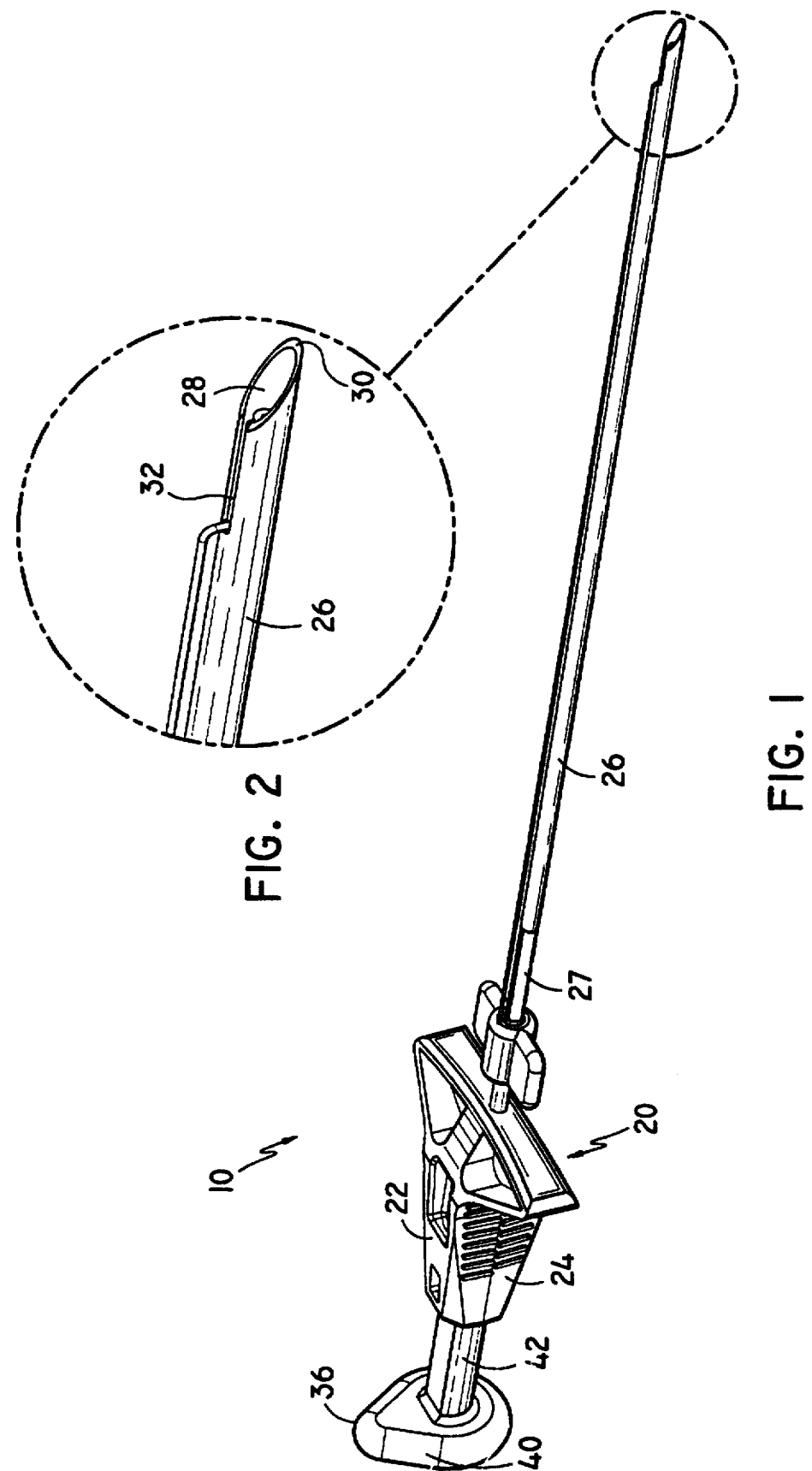

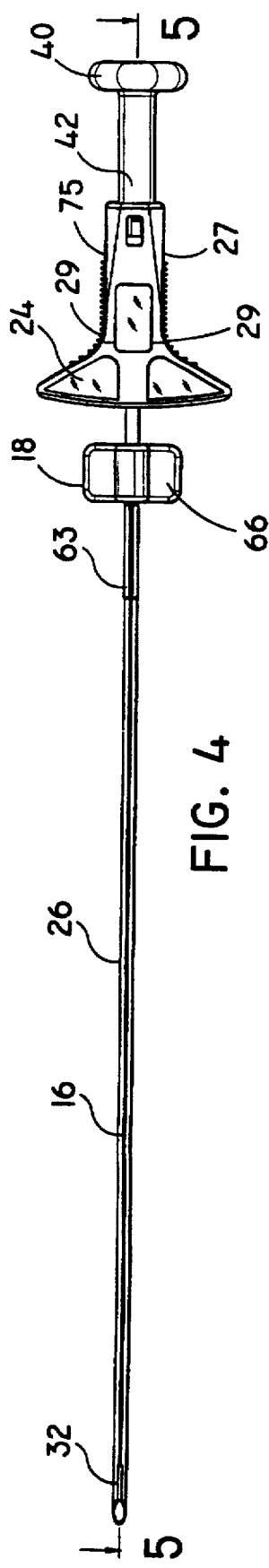
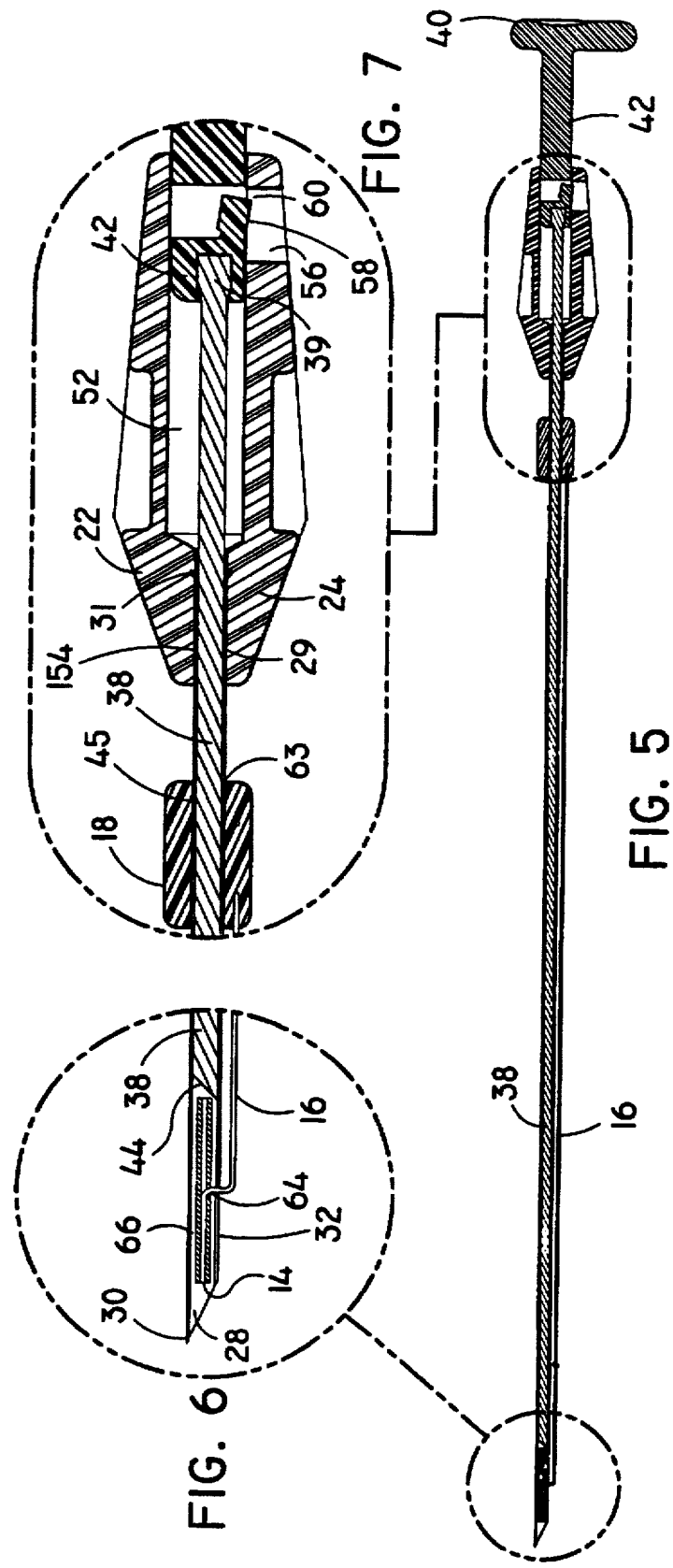
FIG. 4
FIG. 5
FIG. 6
FIG. 7

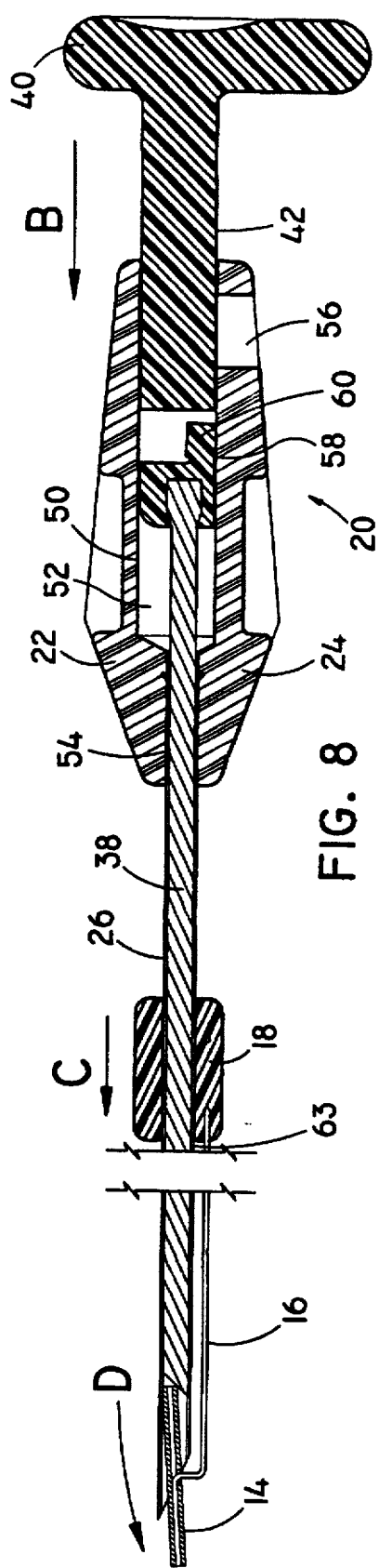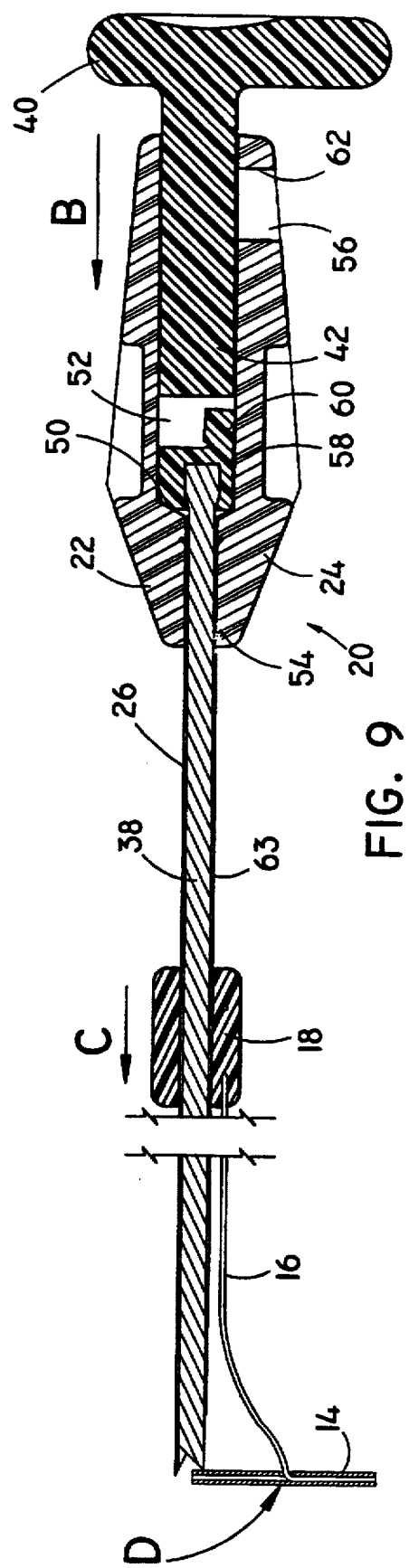

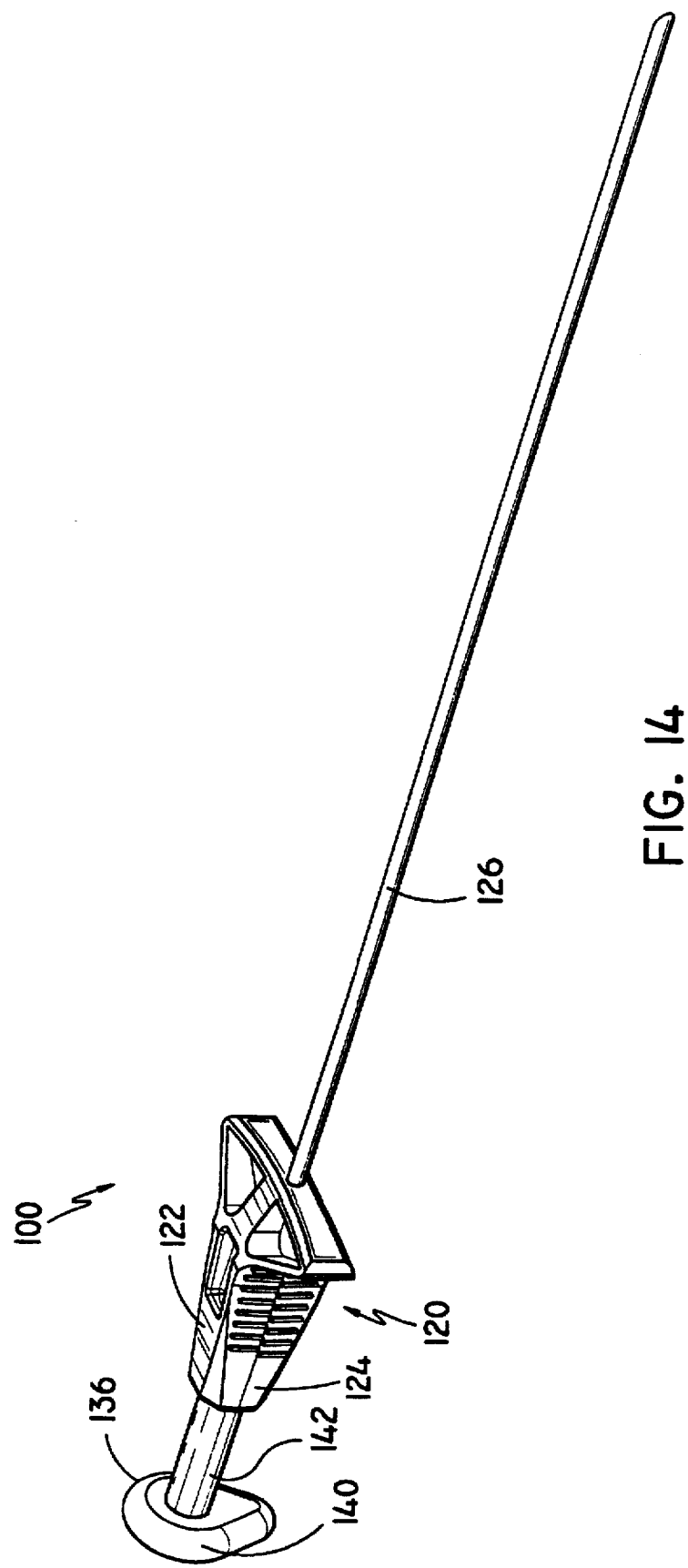

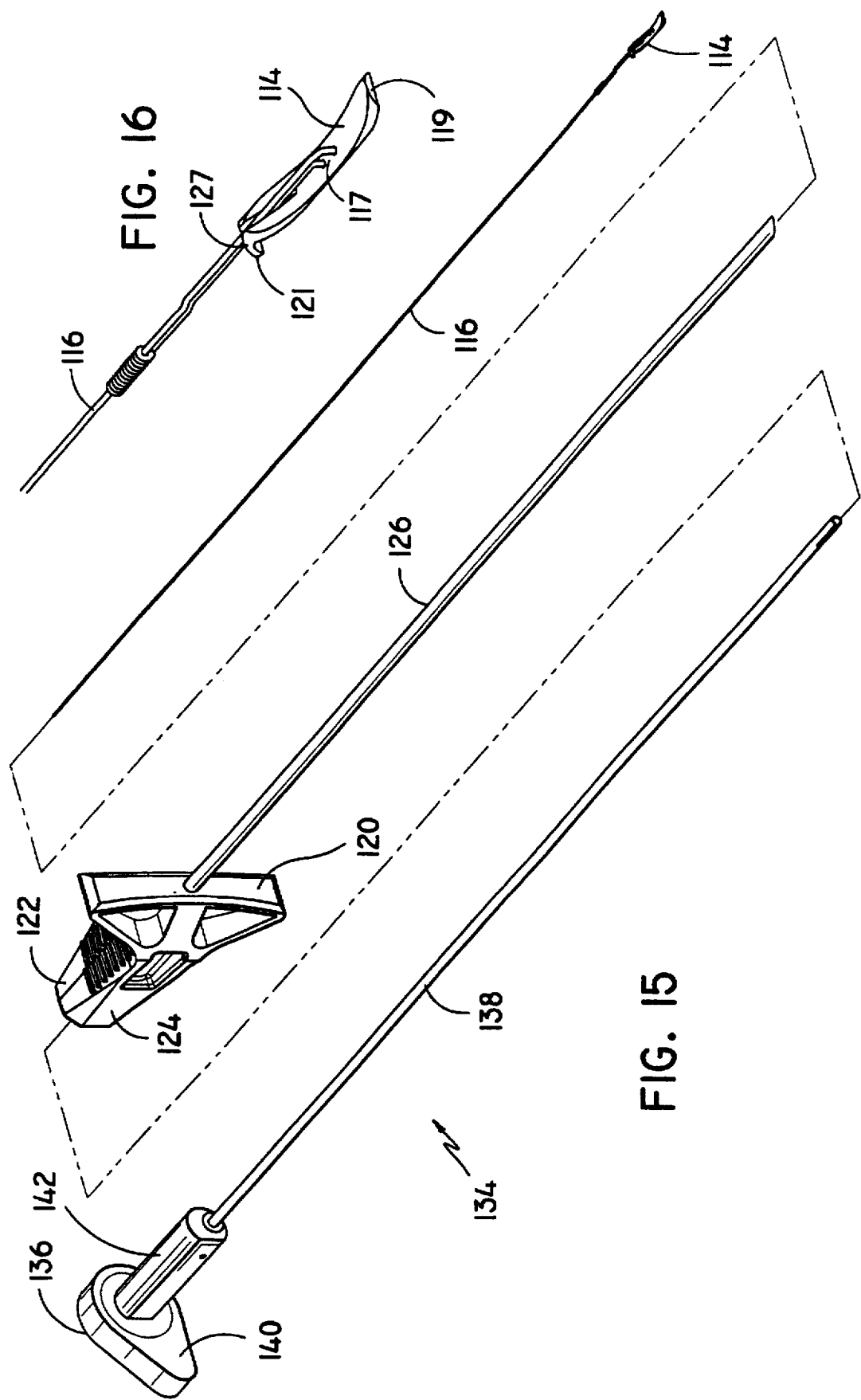

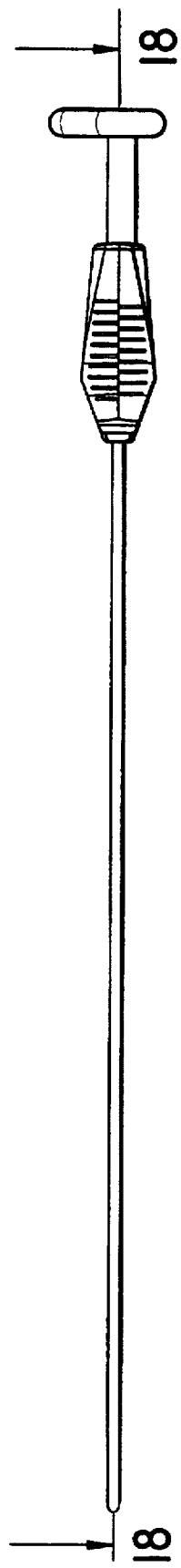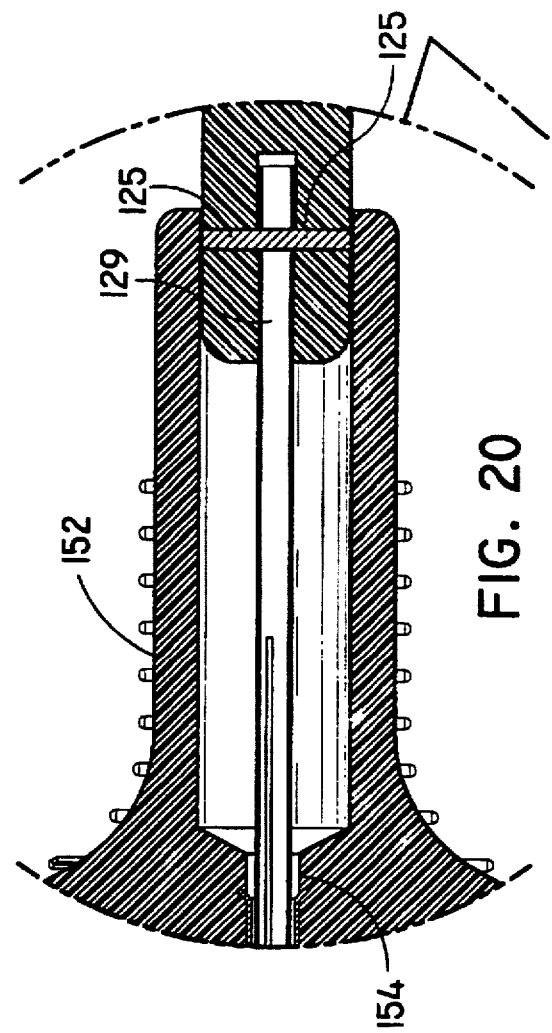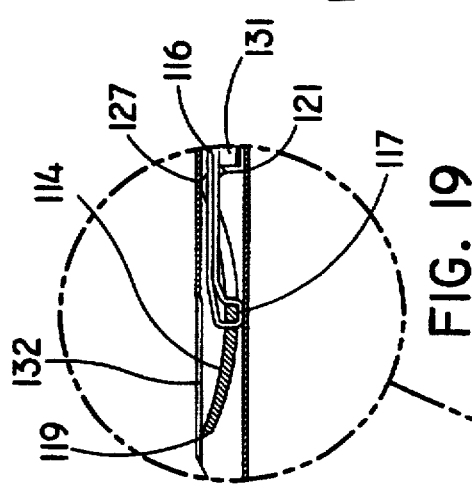

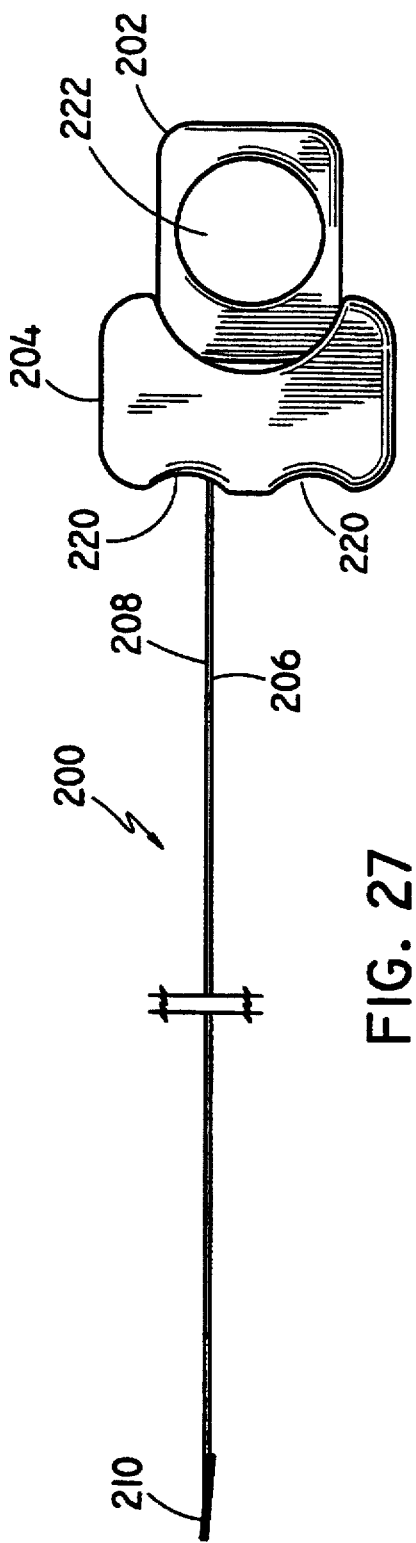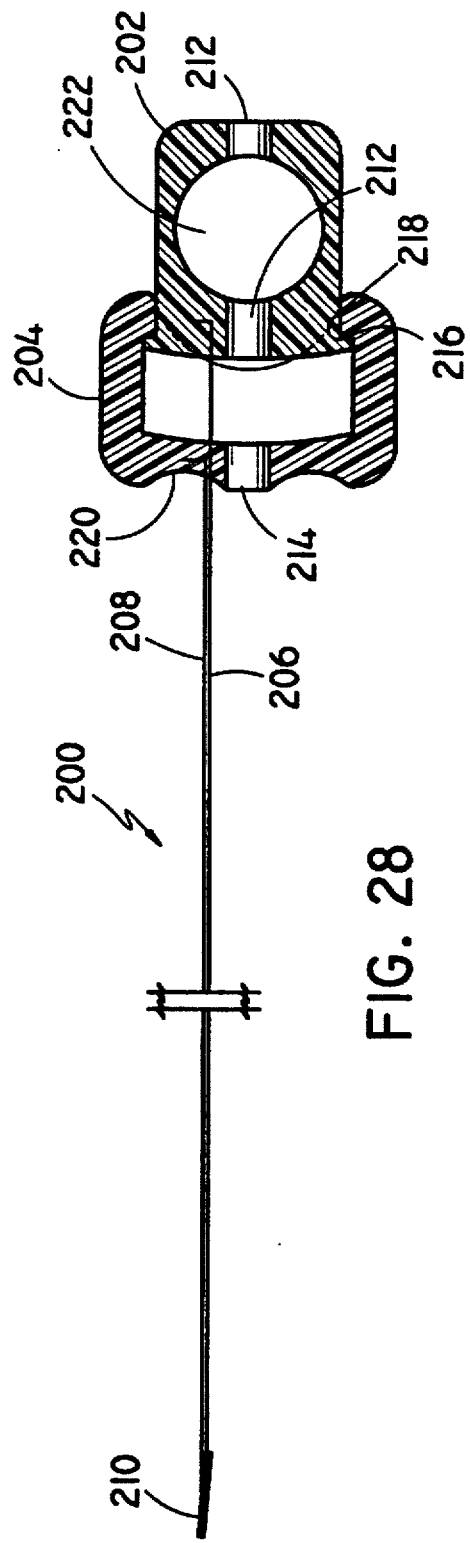

TISSUE TAGGING DEVICE

BACKGROUND

1. Technical Field

The present disclosure relates generally to surgical instruments. More specifically, the present disclosure relates to a tagging device for identifying a particular location within a mass of body tissue.

2. Background of Related Art

Tagging or marking of locations within body tissue, such as non-palpable lesions discovered within the body, and devices such as needles and wires for marking these lesions, are well known in the art. The devices generally comprise a hypodermic needle or cannula which is inserted into the body and positioned adjacent to or in contact with the lesion. The wire marker, which extends beyond the distal end of the cannula, is anchored into or adjacent the lesion so that the lesion is marked for subsequent surgical procedure such as excision or biopsy. After marking the lesion with the wire marker, the cannula may be removed from the body, leaving the wire in place and extending from the body.

In procedures involving marking the location of suspect tissue within the breast, the breast is typically compressed during a mammographic tagging procedure so that after the needle is in place and compression discontinued, it is possible that the needle marker may dislodge or migrate to a different position than the position set during the tagging procedure. Various tissue marking needle systems have been proposed to aid in locating non-palpable lesions within the breast and to prevent inadvertent dislodgment and/or migration of the needle. One such system includes a cannula needle and a wire guide made of a shape memory characteristic material which assumes a J-hook configuration. An example of such a device may be found in U.S. Pat. No. 5,011,473 to Gatturna. The needle is inserted into the breast and advanced to identify the location of the breast lesion. The wire is advanced inwardly allowing the J-hooked end to engage body tissue to immobilize the needle. However, devices utilizing such J-hook systems have been unable to solve the problem of preventing migration of the marker. The needle and the hook device can be displaced if pressure is applied to the breast during transport of the patient or during surgery. Also, if the strength or resiliency of the wire is less than that required to penetrate the lesion, the hook may not reform, allowing the marker to migrate.

Another example of a tissue-marking needle system, commonly referred to as a needle and hook-wire system, may be found in U.S. Pat. No. 5,158,084 to Ghiatas. The tissue-marking needle system includes a stainless steel wire having a hooked-end. Similar to the J-hook system, the needle is inserted into the breast to locate the lesion and the wire is slid through the needle to engage the body tissue to anchor the wire at the breast lesion. However, compression of the breast during mammographic filming of the breast lesion may result in migration or displacement of the needle. Although the hook prevents outward movement of the wire, it does not prevent inward advancement of the wire.

Accordingly, a need exists for an improved tissue tagging device which overcomes the above-noted disadvantages, is easy to use and provides more reliability when marking suspect tissue.

SUMMARY

In accordance with the present disclosure, a tagging device for identifying the location of lesions within body tissue is provided. The device includes an elongated tube or cannula, a body member having a throughbore, a reciprocable actuating assembly, and an anchor assembly. The elongated tube is fastened within the throughbore of the body member and extends distally therefrom. The actuating assembly includes a plunger extending through the body member throughbore and having a first end extending within the elongated tube and a second end having a control knob mounted thereon. The plunger is movable distally into engagement with the anchor assembly, which in a first embodiment includes an anchor, an elongated member and a guide member. The elongated member is fastened between the anchor and the guide member, and the anchor is positioned in the distal end of the elongated tube. The guide member includes a throughbore configured to be slidably positioned about the proximal end of the elongated tube. The proximal end of the tube has an increased diameter section to increase friction with the guide member. In use, the plunger is moved distally via the control knob to engage and move the anchor distally. As the anchor is moved distally, the guide member is pulled by the elongated member over the large diameter section of the tube creating tension in the elongated member. The force on the anchor by the elongated member pivots the anchor as it is being pushed from the tube from a position substantially parallel to a longitudinal axis of the tube to a position substantially perpendicular to the axis of the tube.

After the anchor has been pivoted to the perpendicular position, the guide member will have passed over the large diameter section of the tube, and can be easily slid off of the tube. Since the anchor is positioned perpendicularly to the elongated member, the likelihood of inadvertently displacing the device is greatly reduced.

Thus, at least two distinct advantages may be realized with the disclosed device. First, during real time imaging, the anchor can be actively engaged for immediate and secure lesion localization. Second, during surgery a surgeon can dissect along the path of the elongated member, and thus use it as a guide to the lesion.

In a further embodiment, the anchor assembly includes an anchor having a body that slopes upwardly along the longitudinal axis from its midpoint to its front and rear ends, an elongated member fastened to the midpoint of the anchor, and a tail extending substantially perpendicularly from the upwardly sloping surface formed at the rear end of the anchor. The plunger includes a hollow tube which is moved distally into engagement with the tail to bias the anchor from a position substantially parallel to a longitudinal axis of the tube to a position substantially perpendicular to the longitudinal axis of the hollow tube. As discussed above, by rotating the anchor to a position perpendicular to the axis of the elongated member, the likelihood of inadvertent displacement of the anchor is greatly reduced.

In an additional embodiment, a pair of elongated members are attached to an anchor and are remotely actuable through attachment to handle members that are movable relative to each other. Provision of a pair of elongated members facilitates deployment of the anchor in the target tissue and further permits relocation and/or removal of the anchor, if desired, through reversal of the movements associated with deployment of the anchor. Introduction of the anchor to the target tissue may be accomplished using structures disclosed herein or through other introductory mechanisms, as are known or would be apparent to those of ordinary skill.

BRIEF DESCRIPTION OF THE DRAWINGS

FIG. 1 is a perspective view of one embodiment of the tagging device;

FIG. 2 is an enlarged view of the distal end of the embodiment shown in the indicated area of detail of FIG. 1;

FIG. 4 is a plan view of the embodiment of FIG. 1;

FIG. 5 is a cross-sectional view taken along section line 5—5 of FIG. 1;

FIG. 6 is an enlarged view of the distal end of the tagging device shown in the indicated area of detail of FIG. 5;

FIG. 7 is an enlarged view of the body of the tagging device shown in the indicated area of detail of FIG. 5;

FIG. 8 is a longitudinal cross-sectional view which illustrates initial plunger advancement of the embodiment of the tagging device shown in FIG. 1;

FIG. 9 is a longitudinal cross-sectional view which illustrates full distal advancement of the embodiment of the tagging device shown in FIG. 1;

FIG. 14 is a perspective view of another embodiment of the tagging device;

FIG. 15 is a perspective view with parts separated of the tagging device of FIG. 14;

FIG. 16 is a perspective view of the anchor assembly of the tagging device of FIG. 14;

FIG. 17 is a top view of the tagging device of FIG. 14;

FIG. 18 is a longitudinal cross-sectional view taken along section line 8—8 of FIG. 17;

FIG. 19 is an enlarged view of the distal end of the embodiment of the tagging device shown in the indicated area of detail of FIG. 18;

FIG. 20 is an enlarged view of the proximal end of the body of the embodiment of the tagging device shown in the indicated area of detail of FIG. 18;

FIG. 27 is a side view similar to FIG. 25 with the anchor in a second position; and FIG. 28 is a side view, partially in section, of the tissue marking assembly of FIG. 25, with the anchor in the second position.

DETAILED DESCRIPTION OF PREFERRED EMBODIMENTS

Figure 3:
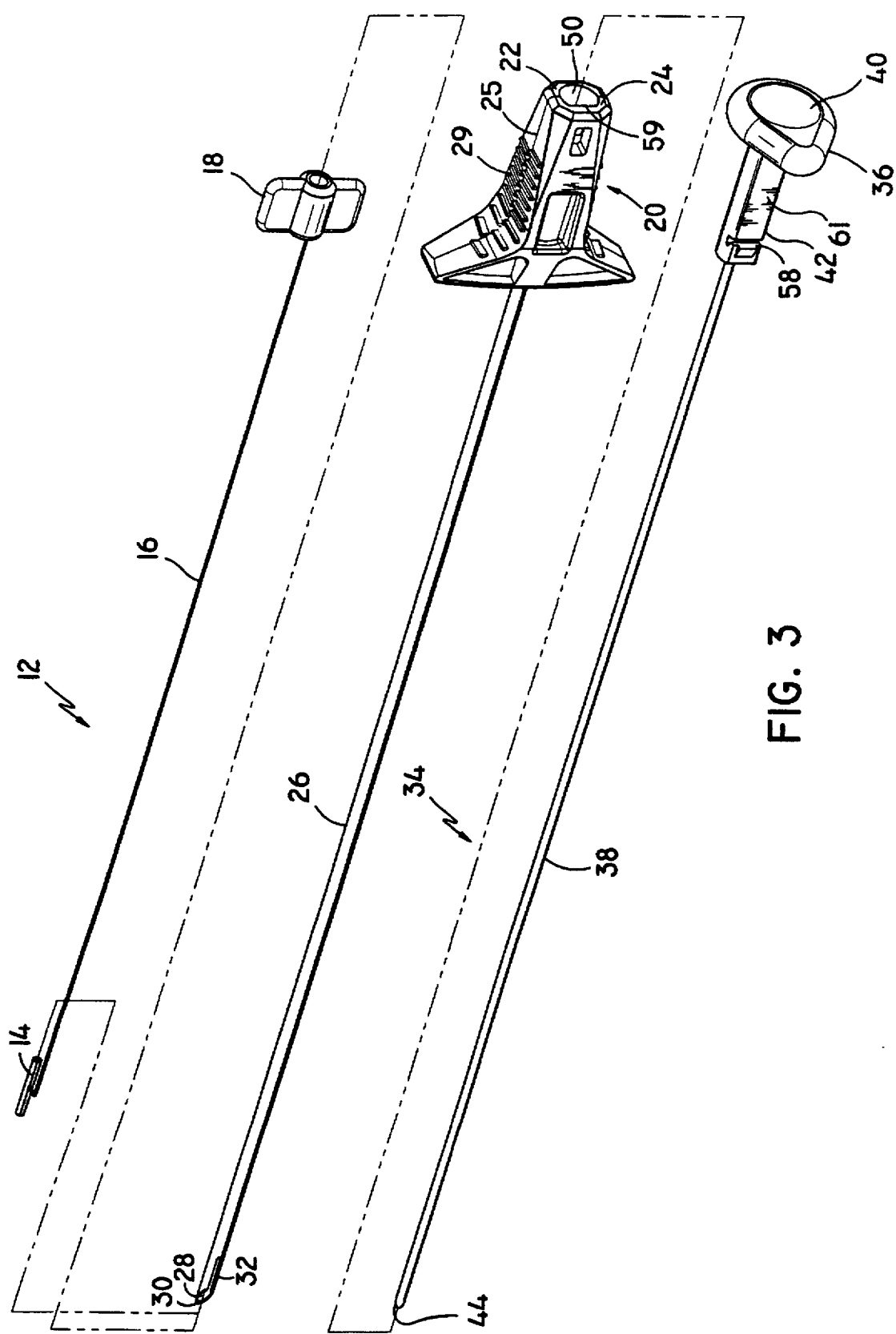
FIG. 3 is a perspective view with parts separated of the embodiment shown in FIG.1.

Preferred embodiments of the presently disclosed tagging device will now be described in detail with reference to the drawings, in which like reference numerals designate identical or corresponding elements in each of the several views.

One embodiment of the presently disclosed tagging device will now be described with reference to FIGS. 1–13. In FIGS. 1 and 2, tagging device 10 generally includes a body 20 formed of first and second body halves 22, 24, an elongated tube 26 extending distally from the body 20, an anchoring assembly 12 supported on the elongated tube 26, and an actuator assembly 34 operably associated with the anchor assembly 12.

Referring to FIG. 3, (also shown in FIGS. 8 and 9) the body 20 defines a stepped throughbore 50 having a first diameter portion 52 and a second smaller diameter portion 54. The first diameter portion 52 opens onto a rear face of the body 22, 24. The second diameter portion 54 is connected to the proximal end of the first diameter portion 52, and opens onto a distal face of the body 20. The body 20 is flared outwardly at its distal end, and includes a pair of sidewalls 25, 27 having spaced vertical ridges 29 formed thereon. The flared distal end and the spaced vertical ridges 29 facilitate grasping and actuation of the device.

The actuator assembly 34 includes an actuator knob 40, an actuator piston 42, and an actuator plunger 38. The actuator piston 42 is configured to be slidably positioned within the first diameter portion 52 of the throughbore 50. A proximal end of the piston 42 extends from the throughbore 50 and is connected to the actuator knob 40. The actuator plunger 38 has a proximal end 39 fastened to the distal end of the piston 42, and a distally extending body portion 41. The distally extending body portion 41 passes through the second diameter portion 54 of the throughbore 50 into the elongated tube 26.

Referring to FIGS. 4–7, the proximal end of the elongated tube 26 is secured within the smaller diameter portion 54 of the throughbore 50. The distally extending body portion of the plunger 38 extends from within the throughbore 50 into the elongated tube 26 and can be reciprocated therein by pressing on the actuator knob 40. To prevent inadvertent proximal movement of the actuator assembly 34 and possible disengagement from the body 20, the actuator piston 42 has a resilient latch member 58 cantilevered thereto positioned to be engaged in an opening 56 formed in the body 24. The latch member 58 includes a free end 60 that projects into the opening 56 when the actuator assembly 34 is in a retracted position. Proximal movement of the actuator 34 beyond the fully retracted position is prevented by engagement between the free end 60 of the latch member 58 and an inner surface 62 of the opening 56. Distal movement of the actuator piston 42 causes a sidewall of the latch member 58 to engage another wall of opening 56 to bias the latch member 58 from within the opening 56 and permit distal movement of the actuator assembly 34.

Referring temporarily back to FIG. 3, the first diameter portion 52 of the throughbore 50 has a planar wall 59. The actuator piston 42 also includes a planar wall 61 configured to slidably engage the planar wall 59 of the throughbore 50 to prevent relative rotation therebetween.

Referring again to FIGS. 4 to 7, anchoring assembly 12 includes an anchor 14, an elongated member 16, for example, wire and a guide member 18. The anchor 14 is configured to be positioned in the distal end of the elongated tube 26, and includes an intermediate opening 64 to facilitate attachment to one end of the elongated member 16. The proximal end of the elongated member 16 is fastened to the guide member 18 which is formed with a cylindrical longitudinal throughbore 45 configured to permit the guide member 18 to be slidably received about the elongated tube 26. A slot 32 is formed in the distal end of the elongated needle 26 to permit the elongated member 16 to communicate directly with the anchor 14. The proximal end of the elongated tube 26 includes a section 63 of increased diameter. The guide member 18 is slidably positioned about the section 63 of increased diameter to increase the frictional fit between the two members.

The distal end of the plunger 38 includes an angled surface 44 that engages the proximal end of the anchor 14 when the plunger is moved distally, and is positioned to pivot the distal end of the anchor 14 about the proximal end of the anchor 14.

Figure 10:
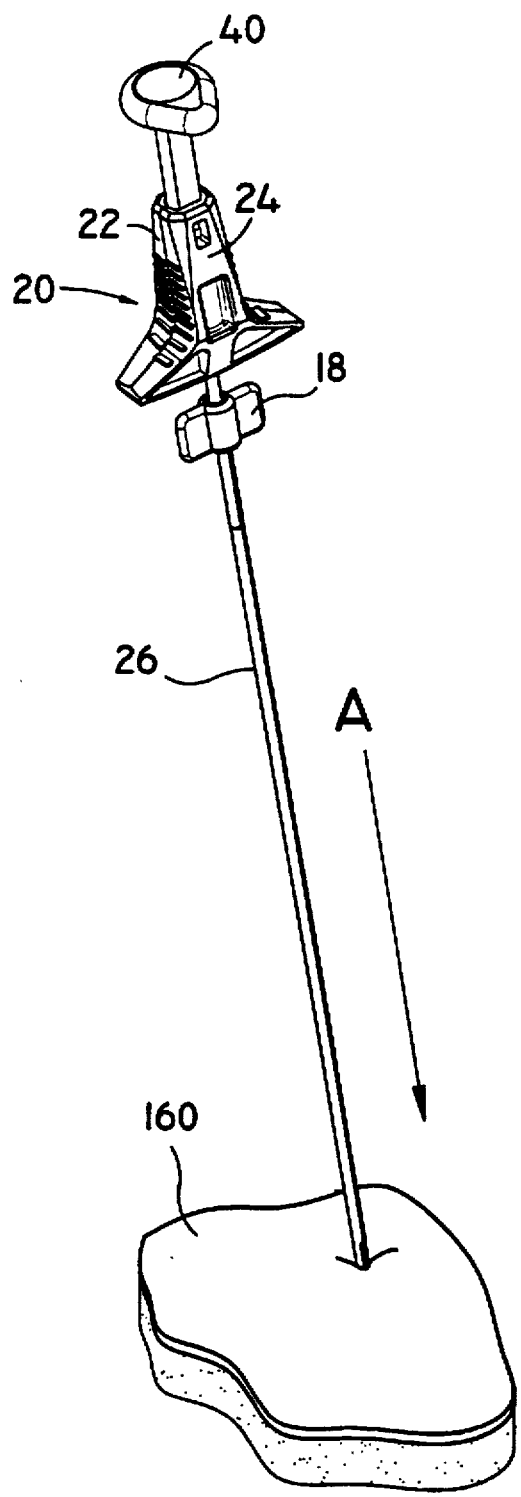
FIG. 10 is a perspective view which illustrates the embodiment of the tagging device shown in FIG. 1 inserted into body tissue in a retracted position of the plunger.
Figure 11:
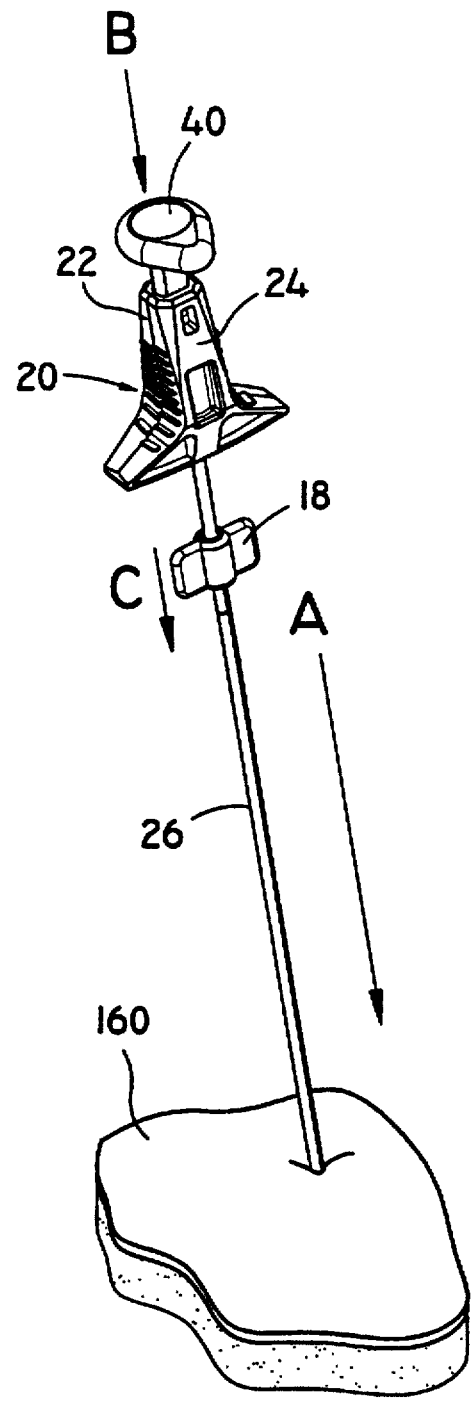
FIG. 11 is a perspective view which illustrates the embodiment of the tagging device shown in FIG. 1 inserted into body tissue in an advanced position of the plunger.

In use, as shown in FIGS. 8-13, elongated tube 26 is positioned to locate a breast lesion, as shown in FIG. 10, by inserting the tagging device 10 as indicated by arrow "A". The location is preferably confirmed using known techniques such as mammographics, stereotactics or X-ray. As shown in FIGS. 8-9 and 11, the tagging device 10 is actuated by grasping the body 20 and pressing down on the actuator knob 40 to move the actuator piston 42 and plunger 38 distally, as indicated by Arrows "B" in FIGS. 8, 9 and 11, into engagement with the anchor 14. As the anchor 14 is pushed distally, elongated member 16 also travels distally. The guide member 18 is thus pulled distally by elongated member 16. However, guide member 18 is positioned on increased diameter portion 63 of the elongated tube 26, and its movement therealong is retarded by friction. Thus, anchor 14 traverses an arcuate path in the direction of Arrow "C" in FIGS. 8, 9 and 11 as plunger 38 moves distally. The anchor 14 is pushed completely from the distal end of the elongated tube 26 and will continue to pivot about the distal tip of the angled surface 44. At this point, the anchor 14 will have been rotated approximately ninety degrees and will be anchored in position marking the lesion site.

Figure 12:
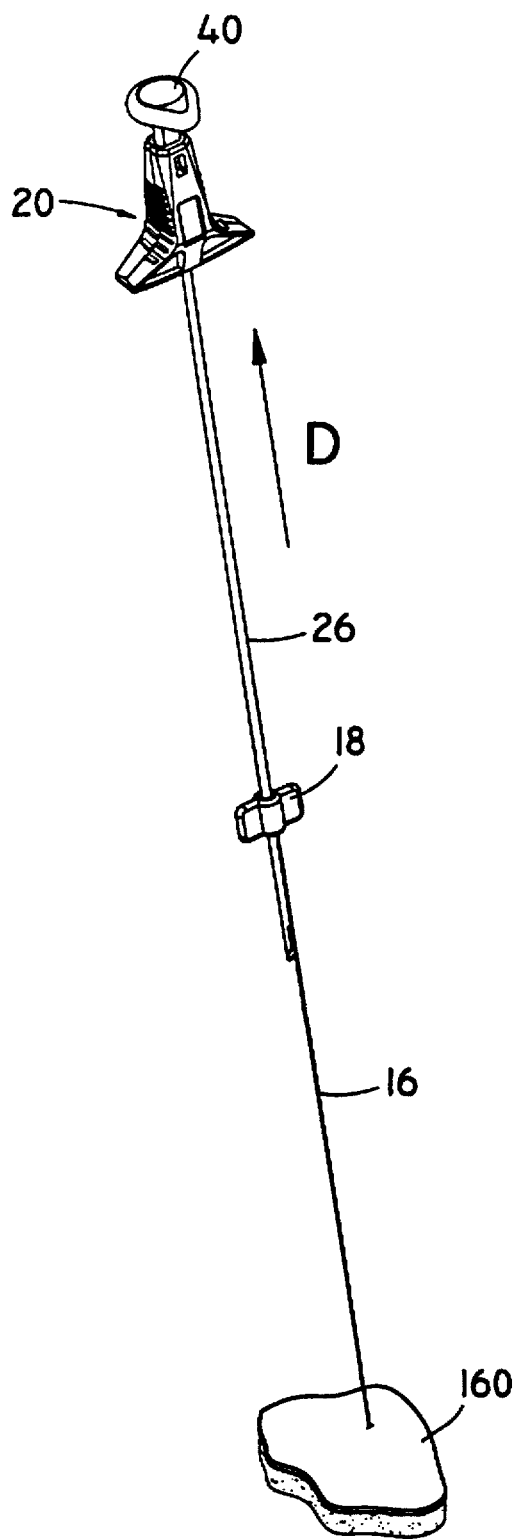
FIG. 12 is a perspective view which illustrates the embodiment of the tagging device shown in FIG. 1 anchored in position with the hollow needle removed from within the body tissue.
Figure 13:
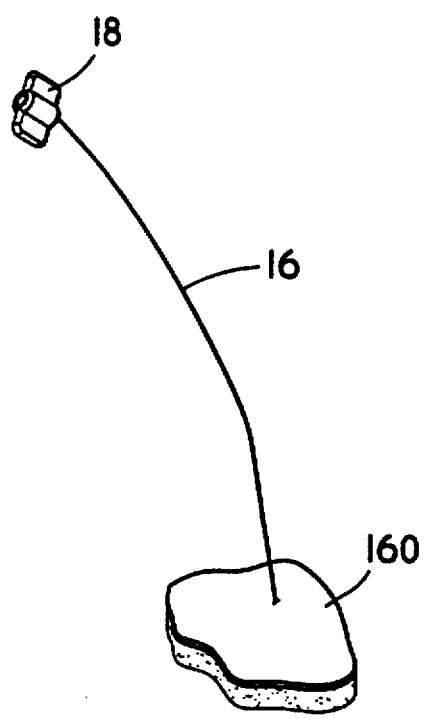
FIG. 13 is a perspective view which illustrates the embodiment of the tagging device shown in FIG. 1 in which the anchoring assembly is detached from the device and secured in position within the body tissue.
Figure 21:
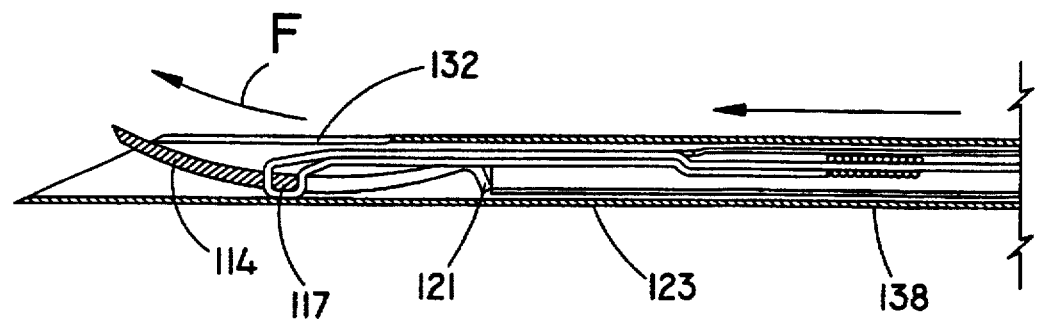
FIG. 21 is a partial side cross-sectional view which illustrates the distal end of the tagging device of FIG. 14 in a retracted plunger position.
Figure 22:
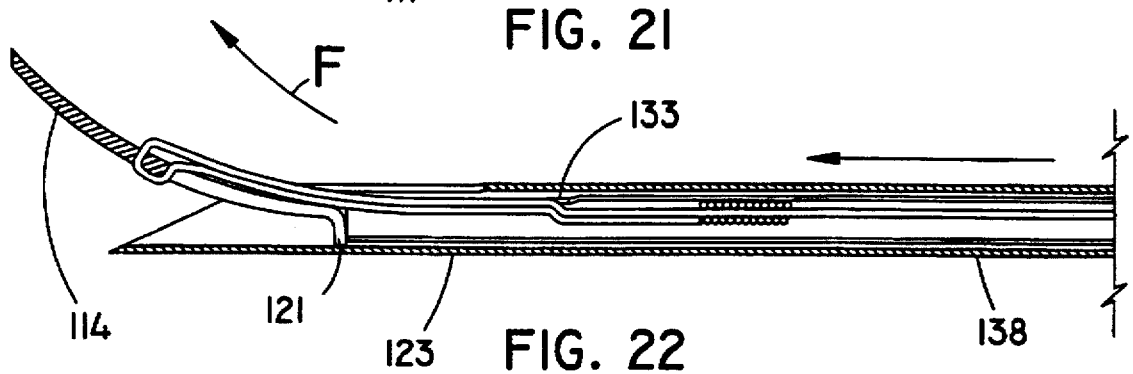
FIG. 22 is a partial side cross-sectional view of the distal end of the tagging device of FIG. 14 which illustrates initial plunger advancement.
Figure 23:
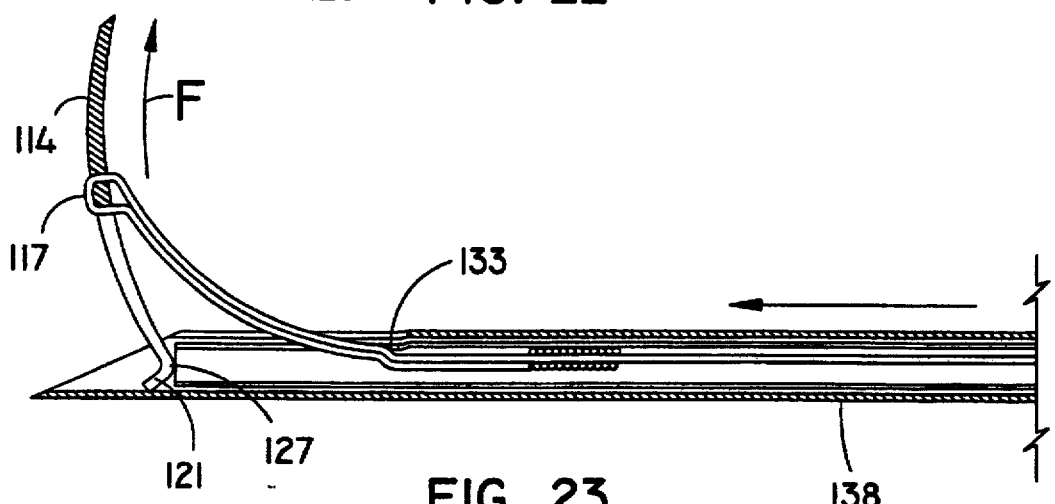
FIG. 23 is a partial side cross-sectional view which illustrates final plunger advancement of the embodiment of the tagging device of FIG. 14.

As illustrated in FIGS. 12 and 13, the guide member 18 can be removed as indicated by Arrow "E" in FIG. 12 from the elongated tube 26 after the anchor 14 has been ejected. The guide member 18 can be slid from the elongated tube 26 easily because the diameter of the elongated tube 26 is not increased towards the distal end of the tube 26.

A further embodiment of the presently disclosed tagging device will now be described with reference to FIGS. 14 to 24. In FIGS. 14 and 15, tagging device 100 includes a body 120 having first and second body halves 122, 124 defining a stepped throughbore 150 having a first diameter portion 152 and a second diameter portion 154. The throughbore 150 is configured to slidably receive a piston 142 and a plunger 138 of an actuation assembly 134. An elongated tube 126 is fastened within the stepped throughbore 150 and extends distally from the body 122, 124. The proximal end of the actuator assembly 134 includes an actuator knob 140 which can be pressed to move the plunger 138 distally within the tube 126. All of the above features have been discussed with reference to the first embodiment and will not be discussed in detail herein.

Referring to FIGS. 16 to 20, an anchor assembly 112 includes an arcuate anchor 114 and an elongated member 116 fastened to a central portion of the anchor 114 at an attachment point 117. The anchor 114 slopes upwardly from the attachment point 117 in the proximal and distal directions along its longitudinal axis. The anchor 114 is formed with a distal end having a tapered surface with an edge 119 and a proximal end having a tail 121 which extends along a curved surface 127 to a position substantially perpendicular to the upwardly sloping proximal end of the anchor 114. The anchor 114 is positioned in the distal end of the tube 126 and the elongated member 116 extends from the attachment point 117 of anchor 114 proximally within the tube 126.

As shown in FIGS. 19 and 20, the plunger 138 is formed from a tube which has a proximal end 129 fastened to the actuator piston 142 via a pin 125 and a distal end 131 positioned to engage the tail 121 of the anchor 114. The anchor 114 is configured to be slidably positioned within the distal end of the tube 126. The tapered surface 119, the curved surface 127 and the attachment point 117 of the anchor frictionally engage inner surfaces of the tube 126 to retain the anchor 114 within the tube 126. The distal ends of the tube 126 and the tubular plunger 138 comprise hollow slots 132 and 133, respectively. Each slot 132, 133 is dimensioned to allow passage of the wire 116 but prevent passage of the anchor 114.

In use, as shown in FIGS. 21 to 24, tube 126 is positioned to locate a breast lesion by inserting the tagging device 100 into body tissue 160 adjacent suspect tissue. The location is preferably confirmed using known techniques such as mammographics, stereotactics or X-ray. The tagging device 100 is actuated by pressing down on the actuator knob 140 to move the actuator piston 142 and plunger 138 distally into engagement with the tail 121 of the anchor 114. Because of the angle of the tail 121 with respect to the plunger 138, the anchor 114 is pivoted, as indicated by Arrow "F" in FIGS. 21 to 23, until the curved surface 127 of the anchor 114 is positioned within the distal end of the plunger 138.

Figure 24:
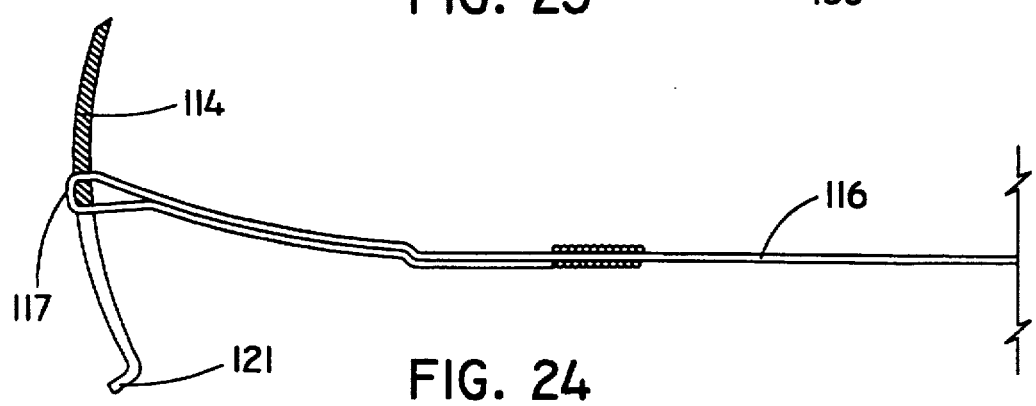
FIG. 24 is a partial side cross-sectional view which illustrates the anchor assembly of the tagging device shown in FIG. 14 in the fully advanced position.

At this point, the anchor 114 will have been rotated to a position substantially perpendicular to the elongated member 116 marking the lesion site. Since the anchor 114 is no longer frictionally held within the tube 126, the tube 126 can be easily separated from the elongated member 116 as shown in FIG. 24 leaving the end of the elongated member 116 extending from the body.

Turning to the alternative embodiment of FIGS. 25-28, tissue marking assembly 200 includes first handle 202, second handle 204, first elongated member 206, second elongated member 208 and anchor 210. The materials of construction of the various components of tissue marking assembly 200 are preferably as described herein for the other embodiments. First elongated member 206 is fixedly attached to first handle 202, while second elongated member 208 is fixedly attached to second handle 204. Both first and second elongated members 206, 208 are fixedly attached to anchor 210 in a spaced relation, as shown. Referring to the partial sectional views of FIGS. 26 and 28, both first and second handles 202, 204 include an internal passage (passages 212 and 214, respectively) which are sized to receive an appropriate structure, e.g., a needle, for introducing the anchor to the target tissue. Thus, internal passages 212, 214 are in axial alignment to facilitate passage of the introducing structure therethrough.

First handle 202 is movable with respect to second handle 204, thereby allowing the user to remotely rotate anchor 210 thorough at least 90°. The degree to which anchor 210 may be remotely rotated may be modified by increasing the degree to which first and second handles 202, 204 are relatively movable. First handle 202 includes an outwardly directed flange 216 which is sized to engage inwardly directed stop 218 on second handle 204, as shown in FIG. 28. Abutment of flange 216 with stop 218 limits the relative movement of first handle 202 relative to second handle 204. In a preferred embodiment, travel of first handle 202 relative to second handle 204 from the position shown in FIGS. 25 and 26 to the position shown in FIGS. 27 and 28 effects a 90° rotation of anchor 210.

Second handle 204 preferably includes finger grips 220 on a distal face thereof, and first handle 202 preferably defines a finger loop 222. Finger grips 220 and finger loop 222 facilitate movement of first handle 202 relative to second handle 204 to effect rotation of anchor 210.

Figure 25:
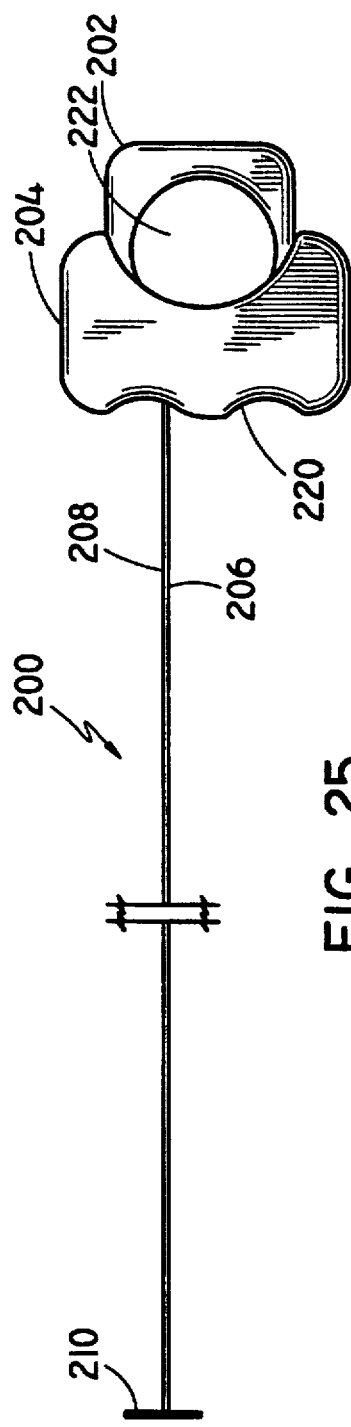
FIG. 25 is a side view of an alternative tissue marking assembly.
Figure 26:
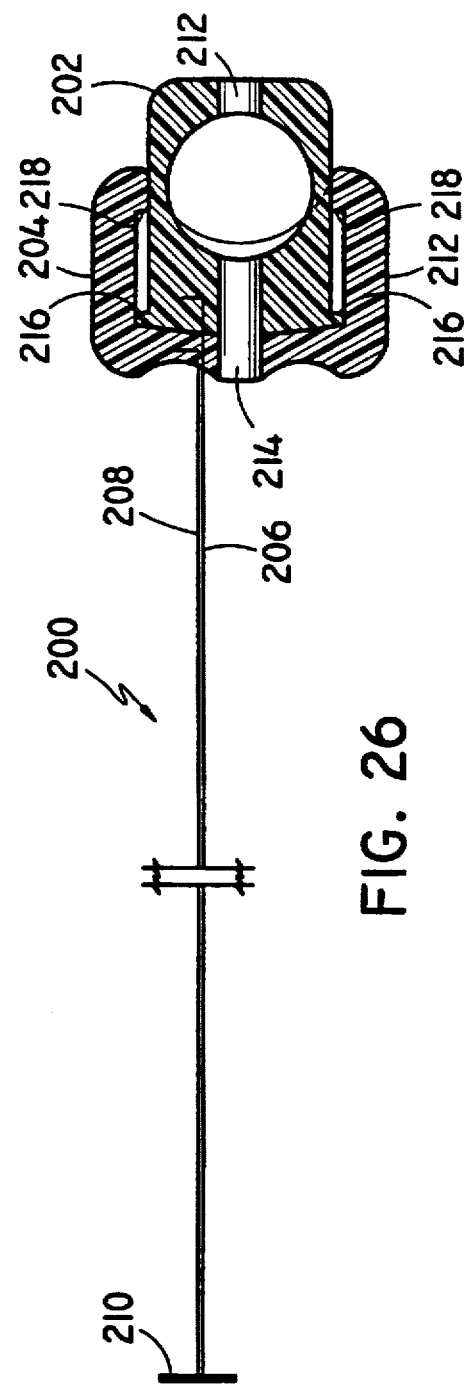
FIG. 26 is a side view, partially in section, of the tissue marking assembly of FIG. 25.

As shown in FIGS. 25 and 26, first handle 202 is in its distal-most position relative to second handle 204. Thus, the operative length of first elongated member 206, which is the length of first elongated member 206 from the finger grips of second handle 204 to anchor 210, is roughly equal to the corresponding operative length of second elongated member 208. Accordingly, anchor 210 is oriented transverse to the longitudinal axis of elongated members 206, 208. As shown in FIGS. 27 and 28, however, first handle 202 is in its proximal-most position relative to second handle 204. In this position, the operative length of first elongated member 206 is substantially less than the operative length of second elongated member 208, thereby effecting rotation of anchor 210 into substantial alignment with the longitudinal axis of elongated members 206, 208.

In use, first and second handles 202, 204 may be repeatedly moved between the relative positions of FIGS. 25, 26 and FIGS. 27, 28, as desired, so as to move anchor 210 between its transverse and longitudinal orientations. In this way, anchor 210 may be introduced (longitudinal orientation), deployed in target tissue (transverse orientation), undeployed (longitudinal orientation) and removed, if desired, or redeployed in the same or a different location (transverse orientation). The ability to deploy and redeploy anchor 210 provides the user with increased flexibility and advantageously improves the user's ability to position anchor 210 in the appropriate tissue.

It will be understood that various modifications may be made to the embodiments disclosed herein. For example, the elongated member need not be made from wire but rather could be made from another strand, fiber, or filament of natural or manufactured material. Therefore, the above description should not be construed as limiting, but merely as exemplifications of preferred embodiments. Those skilled in the art will envision other modifications within the scope and spirit of the claims appended hereto.

What is claimed is:

1. A tagging device for identifying a particular location within a mass of body tissue comprising:

an elongated tube having a proximal end and a distal end;

an anchor releasably positioned within the distal end of the elongated tube;

an elongated member having a first end connected to a central portion of the anchor;

a tension member attached to said elongated tube, said tension member being adapted to hold the elongated member in tension relative to the elongated tube; and a plunger operably engageable with the anchor to move the anchor from a first position within the elongated tube to a second position ejected from the elongated tube;

wherein the plunger and anchor are configured to rotate the anchor as the anchor moves between the first and second positions.

2. A tagging device according to claim 1 wherein the tension member is slidably positioned about and frictionally engages the elongated tube, a second end of the elongated member being connected to the tension member, wherein movement of the anchor from the first position toward the second position causes the tension member to move distally along the elongated tube and wherein the frictional engagement between the tension member and the elongated tube causes further rotation of the anchor.

3. A tagging device according to claim 2 wherein the proximal end of the elongated tube has an increased outside diameter section, the tension member being positioned about the increased diameter section, the distal end of the elongated tube having a smaller diameter section to permit the tension member to be easily removed from the elongated tube after the anchor has been pushed from the elongated tube.

4. A tagging device according to claim 1 wherein the distal end of the elongated tube includes a longitudinal slot, the elongated member being positioned to pass through the slot to connect to the central portion of the anchor.

5. A tagging device according to claim 1 wherein in the first position, a longitudinal axis of the anchor is aligned with a longitudinal axis of the elongated tube and in the second position, the longitudinal axis of the anchor is perpendicular to the longitudinal axis of the elongated tube.

6. A tagging device according to claim 1 further comprising a housing defining a throughbore connected to the proximal end of the elongated tube, the plunger being configured to extend through the throughbore into the elongated tube.

7. A tagging device according to claim 6 wherein the housing includes an opening and the plunger includes a cantilevered latch member, the cantilevered latch member engaging a wall within the housing opening to prevent further retraction of the plunger when the plunger is in a retracted position.

8. A tagging device according to claim 1 wherein the anchor has a main body portion, a first end and a second end, the first end of the anchor having a tail extending at an angle from the main body portion, and wherein the plunger is movable from a retracted position into contact with the tail of the anchor to move the anchor from within the elongated tube.

9. A tagging device according to claim 8 wherein the angle of the tail is such that upon engagement with the plunger, the anchor is continuously rotated as it is moved from the elongated tube from the first position substantially parallel to a longitudinal axis of the elongated tube to the second position substantially perpendicular to the longitudinal axis of the elongated tube.

10. A tagging device according to claim 9 wherein the elongated member is positioned within the elongated tube.

11. A tagging device according to claim 1 wherein the anchor includes a body sloping upwardly from the central portion to first and second ends thereof, and a tail extending at an angle from the second end of the body, the first and second ends of the body and the central portion engaging an inner surface of the elongated tube to retain the anchor within the elongated tube while in a retracted position of the plunger.

12. A tagging device according to claim 1 wherein the anchor comprises a first end tapered to form an edge.

13. A tagging device according to claim 1 wherein the distal end of the elongated tube includes a longitudinal slot formed therein, the slot being configured to permit passage of the elongated member during movement of the anchor.

14. A tagging device for identifying a particular location within a mass of body tissue comprising: an elongated tube having a proximal end and a distal end; an anchor releasably positioned within the distal end of the elongated tube; an elongated member having a first end connected to a central portion of the anchor; and a plunger which defines a hollow tube slidably positioned within the elongated tube, a second end of the elongated member being positioned within the hollow tube, the plunger being operably engageable with the anchor to move the anchor from a first position within the elongated tube to a second position ejected from the elongated tube, the distal end of the hollow tube and of the elongated tube having a longitudinal slot dimensioned to permit passage of the elongated member during movement of the anchor between the first and second positions; and wherein the plunger and anchor are configured to rotate the anchor continuously as the anchor moves between the first and second positions.

15. A tagging device comprising:

an elongated tube having a proximal and a distal end;

an anchor positioned within the elongated tube;

an elongated member extending parallel to and external of the elongated tube, the elongated member having a distal end connected to the anchor and a proximal end connected to the proximal end of the elongated tube.

a plunger movably positioned within the elongated tube from a retracted position to an extended position to engage and move the anchor from a first position within the elongated tube to a second position outside the elongated tube; and wherein the elongated member is connected to the anchor a position to cause the anchor to continuously rotate during movement between the first and second positions.

16. A tagging device comprising:

an elongated tube having a proximal end and a distal end;

an elongated anchor positioned within the elongated tube and having a central portion and a body sloping away from the central portion to first and second ends thereof;

an elongated member having a distal end connected to the central portion of the anchor and a proximal end extending within the elongated tube;

a plunger positioned within the elongated tube and being movable between retracted and extended positions to engage the second end of the anchor and move the anchor from a first position within the elongated tube wherein the anchor is disposed in a first orientation such that one of the ends of the anchor is distal of the central portion and the other end is proximal of the central portion, to a second position outside the elongated tube; and wherein the second end of the anchor is configured to cause rotation of the anchor during movement between the first and second positions.

17. A tagging device according to claim 16 wherein the second end of the anchor includes a tail extending at an angle from the body of the anchor, wherein the plunger engages the tail to cause rotation of the anchor during movement of the anchor between the first and second positions.

18. A tagging device comprising:

(a) a first handle;

(b) a second handle movable relative to the first handle;

(c) a first elongated member fixedly attached to the first handle;

(d) a second elongated member fixedly attached to the second handle; and (e) an anchor, the first and second elongated members being fixedly attached to the anchor in a spaced manner.

19. The tagging device according to claim 18, wherein movement of the first handle relative to the second handle is limited by interacting structures on the first handle and the second handle.

20. The tagging device according to claim 18, wherein the first and second handles form a passage to accommodate passage of a structure for introducing the tagging device to tissue.

21. The tagging device according to claim 20, wherein the structure for introducing the tagging assembly to tissue is a needle.

22. The tagging device according to claim 18, wherein the first and second elongated members define a longitudinal axis and further wherein movement of the first handle relative to the second handle effects movement of the anchor from an orientation substantially aligned with the longitudinal axis to an orientation substantially transverse to the longitudinal axis.

* * * * *